United States Patent [19]
Lewellen et al.

[11] 4,211,673
[45] Jul. 8, 1980

[54] CATALYTIC METAL-RARE EARTH METAL HYDRIDE FOR REDUCTION OF CARBON MONOXIDE IN HYDROGEN

[75] Inventors: Philip C. Lewellen, Albuquerque, N. Mex.; Walter C. Gates, Jr., Newburgh, N.Y.; Roger G. Duranleau, Georgetown, Tex.

[73] Assignee: Texaco Inc., White Plains, N.Y.

[21] Appl. No.: 963,260

[22] Filed: Nov. 24, 1978

[51] Int. Cl.$^2$ .................. B01J 23/10; B01J 23/74
[52] U.S. Cl. ........................ 252/462; 260/449.6 R
[58] Field of Search .................... 252/462; 75/170; 260/449.6 R

[56] References Cited

U.S. PATENT DOCUMENTS

| | | | |
|---|---|---|---|
| 3,918,933 | 11/1975 | Martin | 75/170 X |
| 4,071,473 | 1/1978 | Atkinson et al. | 252/462 |
| 4,142,300 | 3/1979 | Gruen et al. | 75/170 X |

*Primary Examiner*—W. J. Shine
*Attorney, Agent, or Firm*—Robert A. Kulason; Carl G. Ries; Henry W. Archer

[57] ABSTRACT

Disclosed are a catalyst composed of a hydride of a rare earth and a transition metal, such as $LaNi_5$ or $LaCo_5$, and a reaction of $H_2$ and CO to produce oxygenated hydrocarbons catalyzed by this catalyst. The reaction takes place at room temperature and at relatively low pressure.

2 Claims, 2 Drawing Figures

4,211,673

CATALYTIC METAL-RARE EARTH METAL HYDRIDE FOR REDUCTION OF CARBON MONOXIDE IN HYDROGEN

FIELD OF THE INVENTION

This invention relates to novel catalysts composed of a rare earth metal and a transition metal and to their use in the reduction of CO to produce oxygenated hydrocarbons.

DESCRIPTION OF THE PRIOR ART

In U.S. Pat. No. 4,071,473, assigned by G. B. Atkinson and L. J. Nicks to the U.S. Secretary of the Interior, a catalyst prepared from an alloy of one or more of the Group VIII transition metals, e.g., Ni or Co, with yttrium or a rare earth metal is formed by reaction with CO and $H_2$ to oxidize the second metal, prior to its use in hydrocarbon conversion reactions, e.g., the methanation of CO and $H_2$ to produce methane and water vapor. The first named metal comprises from 5 to 95 weight percent of the alloy. The temperatures at which the alloys are treated are above 275° C.

SUMMARY OF THE INVENTION

In accordance with the broad concept of the invention, a catalyst is provided which is characterized by the general formula:

$$RT_5(H)_x$$

where R is a rare earth metal (lanthanum, cerium, neodymium, praseodymium); T is a transition metal of Group VIII such as iron, cobalt or nickel and x is a number ranging from 0.1 to 6, the exact number being defined by RT and the partial pressure of hydrogen under which the powdered catalyst is stored. These numbers are readily determined experimentally or by reference to equilibrium data in the literature.

In accordance with the method aspect of the invention, there is provided a method for converting synthesis gas ($H_2$ and CO) to oxygenated hydrocarbons by passing such gas over the above described catalyst at room temperature and at a low total pressure where $P_{co} + P_{h2} = 100$ psig. The products are isolated from both flow and batch reactor systems by passage of effluent gas and vacuum extraction of reacted catalyst solids through dry or cold traps to freeze out volatile liquids.

DISCLOSURE OF THE INVENTION

The catalysts of the invention are prepared from commercial supplies of $RT_5$ by:

1. Placing 250—300 g. of $RT_5$ as pieces each of 1 or more grams into a screwcap jar;
2. Placing that jar in an autoclave;
3. Evacuating that autoclave to a pressure below 10 mm Hg;
4. Pressuring that autoclave with $H_2$ exceeding 99.9% purity to 3000—4500 psia;
5. Maintaining the $H_2$ pressure in the autoclave for 30 minutes or more;
6. Venting the $H_2$ from the autoclave until the pressure is less than 20 psia;
7. Holding the autoclave in a venting mode for 30 minutes or more;
8. Repeating steps 4 through 7., 8 times to achieve 9 pressure-depressure cycles;
9. Repeating steps 4 through 6., a ninth time;
10. Rapidly opening the autoclave and loosely placing the screwcap on the jar containing the now powdered $RT_5H_x$;
11. Placing the jar in a "dry box" maintained at a pressure slightly above atmospheric with a small flow of dehydrated and essentially $O_2$-free $N_2$;
12. Maintaining the catalyst in the loosely-capped jar in the "dry box" until ready for use;
13. Placing a known quantity of stored catalyst into a reaction vessel which has been first evacuated and then opened in the same "dry box" as contains the jar of stored catalyst;
14. Assembling the reactor in the reaction system; and,
15. Pressurizing the contents of the reactor with hydrogen so that the $RT_5$ becomes "saturated" with hydrogen.

The pressure needed for "saturation" is readily determined from literature descriptions of $RT_5$-$H_2$ equilibria. Typically, an increase of one atmosphere the partial pressure of hydrogen will raise the hydrogen content of $RT_5H_x$ from x being essentially equal to 0 to its saturation value. Beyond the saturation point, large increase in $H_2$ partial pressure cause only small increases in x.

Stated more simply, x is determined by the pseudo-saturation pressure of $RT_5$ at the temperature at which a given catalytic reaction is to take place, wherein small changes in applied $H_2$ partial pressure below the pseudo-saturation pressure cause x to decline rapidly and large changes in applied $H_2$ partial pressure above the pseudo-saturation pressure cause x to increase only slightly.

The following Table lists representative values of T, P, and X for several $RT_5$ equilibria:

| $RT_5$ | °C. | $PH_2$ (atm) | X | Source |
|---|---|---|---|---|
| $LaNi_5$ | 21 | 3 | 5.5 | 1 |
| | 52 | 8 | 5.5 | |
| | 81 | 19 | 4.3 | |
| $SmCo_5$ | 20 | 6 | 2.5 | 1 |
| | 80 | 39 | 2.0 | |
| $CeCo_5$ | 23 | 2 | 2.0 | 2 |
| | 50 | 7 | 1.6 | |
| $LaCo_5$ | 51 | 0.2 | 3.2 | 2 |
| | 91 | 1.5 | 3.0 | |
| $GdCo_5$ | 21 | 25 | 2.2 | 3 |
| $NdCo_5$ | 22 | 0.7 | 2.6 | 3 |
| $PrCo_5$ | 21 | 0.5 | 2.9 | 3 |
| $ThCo_5$ | 21 | 50 | 2.6 | 3 |

1 Philips Res. Repts 25, 133–140 (1970)
2 J. Less-Common Metals 27, 27–34 (1972)
3 Philips Res. Repts. Supp. 1973, No. 2

The above Table is not to be construed as constituting a comprehensive list.

Figure 1:
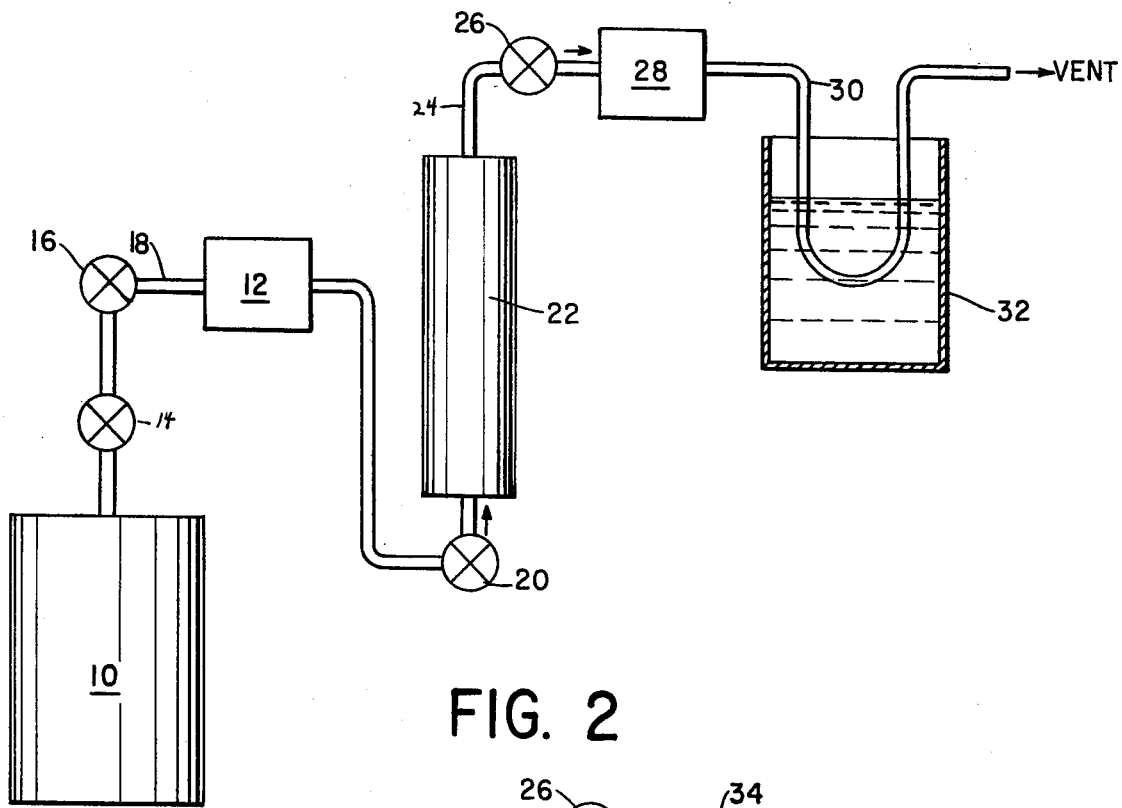
FIG. 1 shows diagrammatically flow apparatus for formation and separation of $LaNi_5H_2CO$ reaction products.

FIG. 1 show the flow apparatus for forming and separating $LaNi_5H_xCO$ reaction products. The apparatus shown includes a stainless steel tank 10 containing synthesis gas which is connected to a Hastings Mass Flowmeter 12 through pipe 18, and metering valves 14 and 16. The synthesis gas then is flowed through valve 20 to the bottom of a jacketed reactor 22 containing about 10 g. catalyst prepared as described above. The unreacted gas and some reaction products exist through pipe 24, valve 26 and into a back pressure regulator 28 from which unreacted gas is vented through tube 30 kept cold by immersion in dry ice/solvent bath 32.

Figure 2:
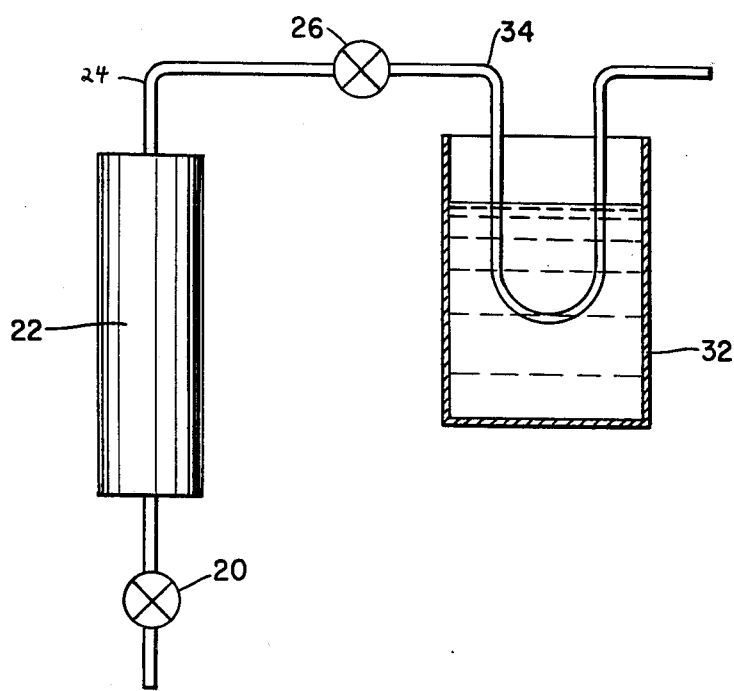
FIG. 2 show schematically apparatus for isolation of the reaction products from $LaNi_5$ solids.

FIG. 2 shows the apparatus modified for isolating the reaction products left on the catayst in reactor 22. Valve 20 is closed and valve 26 is connected, through a glass chromatography tube 34 immersed in a bath of liquid nitrogen, to a vacuum pump. Generally the isolation requires 30 to 45 minutes to collect several fractions of products.

The products of the invention have been analyzed by NMR and where possible by IR spectrometry.

The reaction product from this system appear to be primarily oxygenated hydrocarbons. Acetone, ethanol, methanol, t-butanol and 2,3 dimethyl 2-butane have been identified as reaction products. Several other compounds have been observed via proton NMR spectrometry but have not been identified. In addition, water and elemental carbon have been identified as products.

Product distribution is to some extent a function of CO concentration at constant total pressure. Under pure CO, true catalytic activity is limited; $Ni(CO)_4$ is the only detectable "product". Lower CO concentrations lead to production of a wider range of products. At 50% in $H_2$, acetone, ethanol, and methanol have been detected as products. Formation of these and several other unidentified products has been observed at CO concentrations as low as 0.1%. One particular unidentified product, designated as "X", (characterized by a singlet NMR peak at 1.6) has been produced in fairly large yield under such conditions. Water also becomes a major product as such low CO levels. Further reductions in CO concentrations (to 0.02%) lead to a narrower product distribution, only water and X have been detected under such conditions.

The data in Table 1 illustrate the above conclusions. The table indicates product distribution as a function of experimental conditions, particularly CO concentrations.

Table I

Summary Of Reaction Conditions And Product Data. All Runs Shown Followed H₂ Saturation Of The Sample.

| Type Experiment | Reaction Conditions | | | | | | Reaction Products | | |
|---|---|---|---|---|---|---|---|---|---|
| | Operating Pressure (psia) | % Co In Feed | Approx. Feed Flow Rate (5cc/min) | Reaction Time (hrs.) | Reaction Temp. (°F.) | Method of Product Collection | Identification Or Designation | Characteristic NMR Peak (δ) | Supplemental Information |
| Flow/Many Cycles | 100 | Variable Up To 100% | Variable | Unknown | Variable | Solids Extraction | Unidentified ("X" In Text) | 1.6 | Only Observed Product X Has Characteristic IR Adsorptions At 8.3μ, 3.4μ And Others. |
| Flow/Many Cycles | 100 | Variable Up To 100% | Variable | Unknown | Variable | Solids Extraction | Water | 4.7 | Primary Component via NMR |
| | | | | | | | Unident. Comp. | 1.19 | |
| | | | | | | | | 1.25 | |
| | | | | | | | | 1.6 | Secondary Component via NMR |
| Flow | 100 | 0.1 | 60 | 1 | 70 | Liquid Separation From Off-Gas | Water | 4.7 | Primary Component |
| | | | | | | | Unident. Comp. | 0.6 | |
| | | | | | | | | 1.25 | |
| | | | | | | | | 1.6 | Secondary Component |
| | | | | | | | | Possibly Others | |
| Batch (2 Runs) | 100 | 100 | — | 1 | 70-300 | Solids Extraction | Ni(CO)₄ | None | |
| Flow | 100 | 50 | 70 | 16 | 70 | Liquid Separation From Off-Gas | Acetone | 2.18 | IR = 4.9μ |
| Same Run | ↑ | ↑ | ↑ | ↑ | ↑ | Solids Extraction | Water | 4.7 | Primary Component |
| | | | | | | | Ethanol | 1.25/3.75 | |
| | | | | | | | Methanol | 3.5 | |
| | | | | | | | Acetone | 2.18 | |
| | | | | | | | Unident. Comp. | 1.7 | |
| | | | | | | | | 3.25 | |
| | | | | | | | | 4.18 | |
| | | | | | | | | 4.27 | |
| Flow | 100 | 0.15 | 150 | 16 | 70 | Liquid Separation From Off-Gas | Water | 4.7 | Principal Component |
| | | | | | | | Acetone | 2.18 | Secondary Component |
| | | | | | | | Unident. Comp. | 1.21 | Trace Only |
| | | | | | | | | 1.6 | |
| | | | | | | | | 3.60 | |
| Flow | 100 | 0.02 | 60 | 16 | 70 | Liquid Separation From Off-Gas | Water | 4.7 | Principal Component |
| | | | | | | | Acetone | 2.18 | |
| | | | | | | | Unident. Comp. | 1.6 | Secondary Component |

What is claimed is:
1. A catalyst of the formula:

$$RT_5(H)_x$$

wherein R is a rare earth metal, T is a Group VIII transition metal, x is a number ranging from 0.1 t 6, determined by the pseudo-saturation pressure of $RT_5$ at the temperature at which a given catalytic reaction is to take place wherein small changes in applied $H_2$ partial pressure below the pseudo-saturation pressure cause x to decline rapidly and large changes in applied $H_2$ partial pressure above the pseudo-saturation pressure cause x to increase only slightly.

2. The catalyst of claim 1 wherein T is nickel, cobalt or iron.

* * * * *